(12) United States Patent
Kessel et al.

(10) Patent No.: US 6,399,819 B1
(45) Date of Patent: Jun. 4, 2002

(54) PROCESS FOR PURIFYING CREATINE

(75) Inventors: Knut Kessel, Mannheim; Günter Scherr, Ludwigshafen; Thomas Bogenstätter, Bad Dürkheim; Stefan Orsten, Ellerstadt; Dirk Franke, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/734,028

(22) Filed: Dec. 12, 2000

(30) Foreign Application Priority Data

Dec. 22, 1999 (DE) .......................... 199 62 227

(51) Int. Cl.$^7$ ................... C07C 241/00; C07C 229/00; C07C 277/00
(52) U.S. Cl. .................. 562/560; 562/560; 562/561; 564/230
(58) Field of Search ................. 562/560, 561; 564/230, 241

(56) References Cited

U.S. PATENT DOCUMENTS

| 5,719,319 A | * | 2/1998 | Weiss et al. | |
| 6,093,848 A | | 7/2000 | Griendl et al. | ............... 562/560 |
| 6,143,929 A | | 11/2000 | Kessel et al. | ............... 562/560 |

OTHER PUBLICATIONS

Japanese Abstract JP 59–000 500.

* cited by examiner

*Primary Examiner*—Paul J. Killos
*Assistant Examiner*—Farhad Forohar
(74) *Attorney, Agent, or Firm*—Keil & Weinkauf

(57) ABSTRACT

A process for purifying creatine is described in which the creatine to be purified in the form free of water of crystallization is introduced into a saturated aqueous solution of creatine monohydrate, in which the creatine free of water of crystallization is dissolved with hydration, crystals of creatine monohydrate precipitate from the aqueous solution and these are separated off from the aqueous solution.

8 Claims, 3 Drawing Sheets

PROCESS FOR PURIFYING CREATINE

The amino acid derivative creatine occurs in nature in particular as creatine phosphate in vertebrate muscles. Creatine phosphate acts here as cellular energy source for muscular contraction energy. Creatine is used as a food supplement in the therapy of neuromuscular disorders (for example muscular dystrophy) and in endocrinopathies where there is deficient creatine storage and increased creatine excretion via the urine. In addition to use in culture media and as a flavor intensifier in seasonings, creatine is being used to an increasing extent as a food supplement in sport for increasing the body's performance and in particular in bodybuilding.

Creatine prepared by chemical synthesis or isolated from natural sources generally has impurities which can originate from the isolation process and synthetic process or from the starting materials of creatine synthesis. In view of the high amounts consumed per day, of up to 30 g of creatine, for example by competitive sportspersons, strict requirements must be made as to the purity of the creatine consumed in order to prevent accumulation of impurities. There is therefore a requirement for processes which permit creatine to be provided in a simple manner in very high purity. In addition, in the known preparation processes, the creatine is generally produced in a small particle size which is impractical for further processors and end users. A coarser product would therefore be desirable, since this is less dust-forming and has a reduced tendency toward electrostatic charging and caking.

EP 0 754 679 describes a process for preparing creatine in which cyanamide is reacted with sodium sarcosinate or potassium sarcosinate in water at from 20 to 150° C. and a pH of from 7.0 to 14.0. The resultant creatine precipitates from the aqueous solution as sparingly soluble creatine monohydrate, which is separated off and is then washed with cold or hot water for purification. In addition, the possibility of subsequent recrystallization is indicated.

JP 59-000 500 describes creatine synthesis by continuously introducing O-alkylisourea into an aqueous sarcosine solution at a constantly maintained pH of from 10 to 12 and at from 5 to 25° C. The resultant creatine monohydrate crystals are purified via a sequence of two washing operations using water and methanol. Disadvantageously, during the synthesis spontaneous crystal seed formation occurs and as a result there is high variability of the crystal size and an undesirably high fines content.

DE 197 48 696 describes a process for preparing creatine by O-methylation of urea and reaction of the resultant O-methylisourea salt with sodium sarcosinate. The resultant creatine monohydrate crystals are washed with water or ice-water.

In the preparation process of DE-A-198 60 048.8, an aqueous solution of O-alkylisourea and an aqueous solution of sarcosinate are reacted in the presence of previously introduced creatine monohydrate crystals. The resultant creatine monohydrate crystals are also washed with cold or warm water here.

The subsequent wash operations common to these preparation processes have the disadvantage that only superficially adherent impurities are removed, whereas the impurities incorporated into the crystals at a molecular level or included in the crystals in the form of droplets of the mother liquor remain substantially unaffected.

Recrystallization does offer the opportunity of achieving a higher degree of purity and, in addition, setting the crystal size more precisely. In this process the substance to be purified is dissolved with heating in a solvent, for example water, and crystallizes out from the solution in a purer form on cooling. The saturated solution obtained after separating off the crystals in which the dissolved impurities remain is generally termed "mother liquor". However, the recrystallization of creatine from water is difficult in that not only the absolute solubility but also the temperature dependence of the solubility of creatine in water are low. The solubility of creatine in water is, for example, only about 1% at 0° C. and about 9% at 80° C. In addition, the temperature difference between the dissolution process and crystallization process cannot be increased as desired, since above a temperature of about 80° C., the decomposition of creatine to form breakdown products such as creatinine and N-methylhydantoin, increases to a level which is no longer acceptable. In conclusion, for the recrystallization of creatine from water, generally at least 12 parts by weight of water are required per part by weight of creatine. Therefore, a large volume of mother liquor is produced which must be worked up or disposed of. To obtain larger crystals, typically slow cooling is required during the recrystallization.

Recrystallization from solvents other than water in which creatine is more soluble and the solubility is more dependent on temperature is not described in the literature. When organic solvents are used, in addition, the problem of residue-free disposal of the solvent would occur.

It is an object of the present invention, therefore, to specify a process for purifying creatine, which process does not have said disadvantages.

We have found that this object is achieved, surprisingly, by a purification process which can be carried out economically on an industrial scale and which simultaneously also permits targeted influencing of the crystal size, which process exploits the thermodynamically favored conversion of creatine free of water of crystallization to form creatine monohydrate.

The invention therefore relates to a process for purifying creatine in which the creatine to be purified (also termed "crude creatine" hereinafter) in the form free of water of crystallization is introduced into a saturated aqueous solution of creatine monohydrate, in which the creatine free of water of crystallization is dissolved with hydration, crystals of creatine monohydrate precipitate from the aqueous solution and these are separated off from the aqueous solution.

Creatine free of water of crystallization is in the present case any form of creatine which is deficient in water of crystallization compared with creatine monohydrate, in particular forms which contain, per mol of creatine, less than 0.3 mol, preferably less than 0.05 mol, of water of crystallization.

Crude creatine generally has—without taking into account the content of water of crystallization—a purity of greater than 95%, preferably greater than 98%, for example up to 99.5%. The difference from 100% is formed by impurities which can be of inorganic nature, such as salts, for example sodium chloride or sodium sulfate, or of organic nature, such as urea, dicyandiamide, creatinine, guanidine, N-methylhydantoin, N-methylhydantoic acid, methyliminodiacetic acid, sarcosine or salts thereof. The impurities are generally water soluble. The crude creatine free of water of crystallization is preferably used in finely divided form, for example having a mean particle size of less than 10 μm, in particular less than 5 μm, which may be present in agglomerated form. The small particle size ensures complete dissolution of the particles. If the particles are larger, under some circumstances there is the risk that a skin of sparingly soluble creatine monohydrate rapidly forms which will delay or prevent further dissolution of the particles.

The crude creatine free of water of crystallization is generally produced from the creatine monohydrate (crude creatine monohydrate), which is primarily obtained, for example, as a chemical synthesis product, by drying, for example in a shelf drier, belt drier or by pneumatic transport in a hot-air stream at temperatures of preferably up to 80° C. The drying can be performed at atmospheric pressure or under reduced pressure. During the drying the water of crystallization escapes from the layers of the crystal structure of the creatine monohydrate, the crystals develop cracks in the course of this which are parallel to the layers and finally disintegrate completely to form an amorphous powder (H. Mendel, D. C. Hodgkin, Acta Cryst. 7, 1954, 443–6; C. S. Frampton, C. C. Wilson, N. Shankland, A. J. Florence, J. Chem. Soc., Faraday Trans. 93(10), 1997, 1875–9).

Another possible method of converting the crude creatine monohydrate into crude creatine free of water of crystallization is to admix the crude creatine monohydrate with a solvent, such as ethanol or toluene, that forms an azeotrope with water, and to eliminate the water of crystallization by azeotropic distillation.

Crude creatine is generally prepared industrially by guanylation of sarcosine, that is to say transfer of the guanyl residue (carbamimidoyl residue) to sarcosine or salts thereof. Guanylating agents which can be used are O-alkylisourea salts, in particular O-methylurea methyl sulfate, (cf. JP 59-000 500, DE 197 48 696 or DE-A 198 60 048.8) or cyanamide (cf. EP 0 754 679). Generally, commercial chemicals of technical-grade purity are used in these processes, for example technical-grade solutions of potassium sarcosinate or sodium sarcosinate of a purity of from 85 to 90% by weight. Technical-grade cyanamide solutions generally contain about 5% of dicyandiamide. The impurities present in these chemicals reoccur in part in the crude creatine.

In aqueous solution, the creatine molecule is present in an association with a hydrate shell of a variable number of water molecules. During crystallization from aqueous solution, creatine crystallizes with one mole of water of crystallization, that is to say as creatine monohydrate. The term "saturated aqueous solution of creatine monohydrate" used above means an aqueous solution which is saturated with respect to creatine monohydrate and in which hydrated creatine molecules are present. The aqueous solution can contain as solvent only water or a mixture of water with, for example, up to 70% by weight, preferably up to 30% by weight, of water-miscible organic solvents, such as $C_1$–$C_4$-alkanols, in particular ethanol. The saturated aqueous solution of creatine monohydrate can be charged in advance or prepared in situ by introducing crude creatine free of water of crystallization into water or into a water/solvent mixture, during which, firstly, an amount of the creatine dissolves until the saturation concentration is reached. The addition of further crude creatine free of water of crystallization then leads to the formation of creatine monohydrate crystals.

The weight ratio of anhydrous crude creatine to saturated aqueous creatine monohydrate solution (that is, water or water/solvent mixture from which a saturated solution of creatine monohydrate is formed in situ by a partial dissolution of creatine) can be varied within broad limits with the upper limit only being that the suspension of creatine monohydrate crystals which forms still has a stirrable consistency. It is generally from 1:15 to 1:2, preferably from 1:5 to 1:2.5. In the case of the continuous procedure, the ratios specified apply to the amounts of crude creatine free of water of crystallization and water or water/solvent mixture fed per unit time. Thus in the process of the invention a considerably lower water usage or solvent usage is necessary than with recrystallization. Therefore, in addition, a reduced amount of mother liquor is formed.

In the process of the invention, dissolution of the crude creatine free of water of crystallization in an aqueous phase and precipitation of crystalline creatine monohydrate from the aqueous phase take place in parallel. The process is based on (1) the relatively high water solubility of anhydrous creatine, (2) the ready hydration of creatine free of water of crystallization with formation of a hydrate shell and (3) the relatively low water solubility of creatine monohydrate. The impurities present in the crude creatine are diluted during the dissolution of the crude creatine free of water of crystallization. The impurities are present at low concentration and are generally more water-soluble than creatine monohydrate so that they predominantly remain in the aqueous solution. If the highest possible purity is sought, in the process of the invention, preferably, a high weight ratio of water or water/solvent mixture to crude creatine free of water of crystallization introduced is selected.

In the presence of water, creatine monohydrate is the more thermodynamically favored form compared with the form free of water of crystallization; the negative free enthalpy of hydration of creatine free of water of crystallization is the driving force of the process of the invention. In the case of finely divided crude creatine free of water of crystallization, the conversion to crystalline creatine monohydrate is associated with a decrease in specific surface area. The decrease in surface energy caused as a result makes an additional contribution to the driving force of the conversion. On account of the lower solubility of creatine monohydrate, after reaching the saturation concentration, creatine monohydrate crystals are precipitated in parallel with the introduction of crude creatine free of water of crystallization.

Frequently, the crystallization of creatine monohydrate does not begin spontaneously after the saturation concentration is exceeded. Only above a certain supersaturation does spontaneous nucleation and precipitation of creatine monohydrate crystals occur. These processes are called uncontrolled crystallization processes. Uncontrolled crystallization processes are disadvantageous to the extent that, during the intensive and rapid formation of crystal nuclei, inclusions of mother liquor in the crystals are possible and the crystal size cannot be controlled well. To avoid these disadvantages it is preferred to introduce the crude creatine free of water of crystallization into a suspension of creatine monohydrate seed crystals. The presence of seed crystals abolishes the delay in crystallization. In the case of the batchwise procedure, expediently, creatine monohydrate seed crystals are suspended in a saturated aqueous solution of creatine monohydrate, and the crude creatine free of water of crystallization is introduced into the suspension. In the case of the continuous procedure, the process is expediently controlled in such a manner that some of the creatine monohydrate crystals already formed are always left in the reactor and act as seed crystals for the growth of further creatine monohydrate.

The crude creatine free of water of crystallization is preferably contacted with the saturated aqueous solution of creatine monohydrate with agitation, for example by stirring using suitable stirring means.

The introduction of the crude creatine free of water of crystallization and/or the removal of the creatine monohydrate crystals can optionally be performed continuously or batchwise. In a particularly preferred embodiment of the process, a saturated aqueous solution of creatine monohydrate is charged into a reactor into which water, or a mixture of water with a water-miscible organic solvent, and crude creatine free of water of crystallization are introduced continuously in parallel in a constant ratio and a suspension of creatine monohydrate crystals is discharged continuously.

The process can be carried out, for example, in a loop reactor, stirred tank or in a tank cascade.

Preferably, use is made of a two-stage or multistage arrangement having at least one dissolution and hydration reactor, in which the crude creatine free of water of crystallization is contacted with the aqueous suspension of creatine monohydrate crystals, and at least one post-crystallization reactor, in which the crystals continue to grow and mature. The product stream from the dissolution and hydration reactor to the post-crystallization reactor can be periodic or continuous, preferably with suitable measures being taken to prevent undissolved crude creatine free of water of crystallization from passing into the post-crystallization reactor. From the post-crystallization reactor, a suspension of creatine monohydrate crystals is taken off continuously or periodically, from which suspension the crystals are separated off, for example by filtration or centrifugation. The mother liquor remaining after separating off the crystals contains the impurities introduced together with the crude creatine; it is passed out of the process to prevent an accumulation of the impurities in the process. The water or water/solvent mixture removed together with the mother liquor which is passed out is replaced by continuous or periodic additions of water or water/solvent mixture to the dissolution and hydration reactor.

The dissolution and hydration step of the process of the invention is preferably carried out at from 25 to 75° C., in particular from 40 to 60° C., particularly preferably about 50° C. Although higher temperatures accelerate the dissolution and hydration of the crude creatine free of water of crystallization, they lead to the partial decomposition of the creatine to form creatinine and to losses of yield because of the higher solubility of creatine monohydrate at the higher temperature.

When a post-crystallization reactor is used, a lower temperature is preferably set in this than in the dissolution and hydration reactor, in order to achieve a more complete precipitation of the dissolved creatine monohydrate. In the post-crystallization reactor, for example, a temperature of from 5 to 20° C. can suitably be set.

The further, downstream treatment of the creatine monohydrate crystal suspension taken off from the reactor, in particular the separation of the creatine monohydrate crystals from the saturated aqueous solution of creatine monohydrate, is preferably performed at a temperature which is not lower than the temperature in the dissolution and hydration reactor or in the post-crystallization reactor, if one is used, in order to avoid the delayed precipitation of crystals on contact with vessel walls or filter elements etc.

By selecting the temperature and residence time, the crystal size of the creatine monohydrate produced by the process of the invention can be controlled within broad limits. At a higher temperature, generally larger crystals are obtained. Preferably, a mean crystal size of from 200 to 600 $\mu$m, preferably from 250 to 500 $\mu$m, is set.

The creatine monohydrate crystals separated off can be washed with cold or warm water and/or water-miscible organic solvents to remove adherent residues of mother liquor. They can then be dried in a conventional manner.

The saturated aqueous creatine monohydrate solution (mother liquor) which is obtained after separating off the creatine monohydrate crystals and which contains the crude creatine impurities can advantageously be used as aqueous reaction medium for the guanylation of sarcosine, for example to predilute the starting materials in the process of synthesizing the creatine to be purified. In addition, it can be used as wash liquid for washing the crude creatine monohydrate obtained in the synthesis process. These uses can keep low the material losses of water, solvent, if one is used, and creatine. If the saturated aqueous solution has a high content of water-miscible organic solvents, the mother liquor is preferably not used as reaction medium for the guanylation, but only for washing the crude creatine monohydrate obtained in the synthesis process.

The present invention therefore also relates to a process for preparing creatine monohydrate in which a) sarcosine is reacted in an aqueous medium with a guanylating agent, crude creatine monohydrate separating out, b) the crude creatine monohydrate is separated off from the aqueous medium, c) the crude creatine monohydrate which is separated off is, if appropriate, washed with a wash liquid, d) the crude creatine monohydrate is converted into creatine free of water of crystallization, e) the creatine free of water of crystallization is introduced into a saturated aqueous creatine monohydrate solution, the creatine free of water of crystallization being dissolved with hydration and creatine monohydrate crystals separating out, f) the creatine monohydrate crystals are separated off from the aqueous solution and the aqueous solution separated off is used at least in part as aqueous medium in step a) and/or as wash liquid in step c).

Suitable guanylating agents are those mentioned above. The sarcosine is preferably used in the form of its sodium or potassium salt.

The process of the invention is described in more detail by the accompanying drawings and the examples hereinafter.

Figure 1:
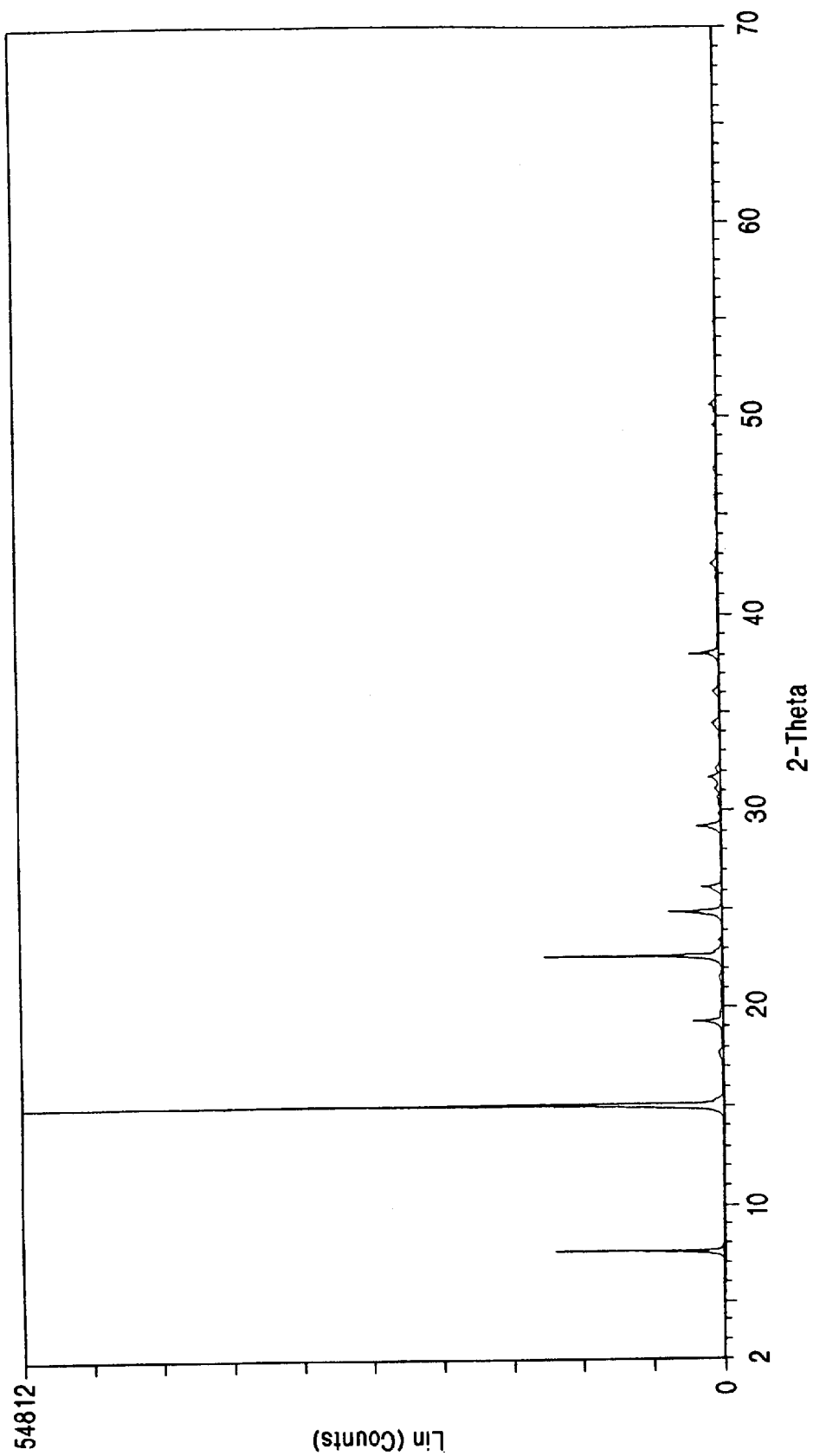
FIG. 1 shows an x-ray diffractogram of crude creatine monohydrate crystals which were obtained by reacting sodium sarcosinate with O-methylisourea methyl sulfate in aqueous solution.
Figure 2:
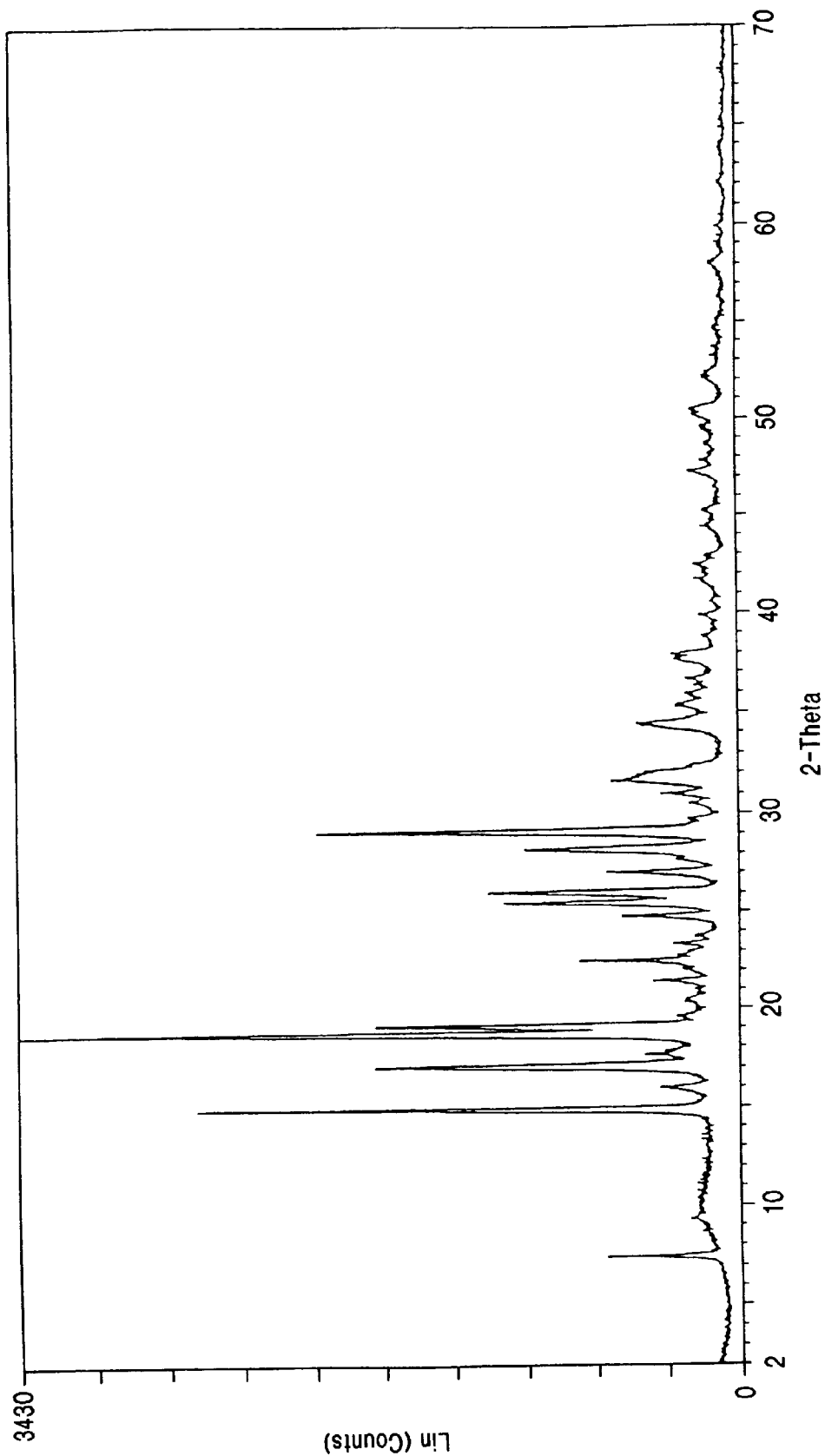
FIG. 2 shows an x-ray diffractogram of crude creatine free of water of crystallization (water content about 0.5% by weight).
Figure 3:
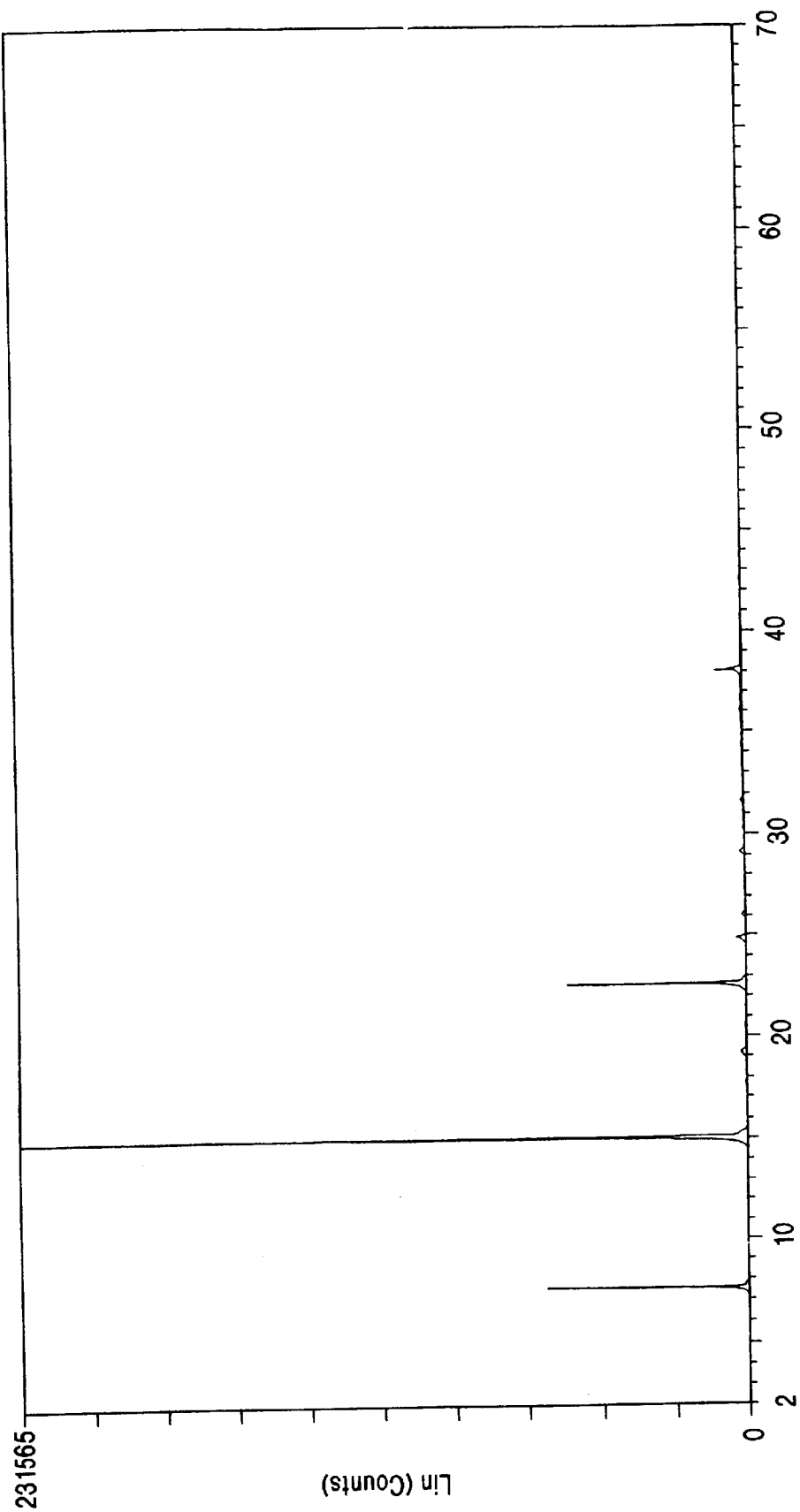
FIG. 3 shows an x-ray diffractogram of creatine monohydrate which was purified by the process of the invention.

The diffractogram of FIG. 3 shows, compared with the diffractogram of FIG. 1, a lower number of bands with higher band sharpness. This indicates a higher crystallinity of the creatine monohydrate treated according to the invention. The diffractogram of FIG. 2 shows numerous bands of low intensity. This indicates that the crude creatine free of water of crystallization is substantially amorphous except for a "residual structure".

EXAMPLE 1

In a 2000 ml jacketed flat-flange flask equipped with a stirrer, 500 ml of drinking water were heated to 50° C. and solid creatine monohydrate was added up to the solubility limit. Via a Dosimat, drinking water was added at a metering rate of 1.88 ml/min; in addition, via a vapor barrier, 0.70 g/min of anhydrous creatine having a dicyandiamide content of 330 ppm (residual moisture below 0.1%) in the form of about 3 $\mu$m particles was added by means of a metering screw. As soon as the filling level reached a volume of 1500 ml, the roughly 30% strength warm suspension of creatine monohydrate flowed at intervals into a jacketed flat-flange flask which was situated below and was kept at 15° C. by a cryostat. A mean residence time of 10 hours resulted from the volume and metering rate. As soon as a filling level of 1500 ml was also reached in this 2000 ml apparatus, the material flowed off at intervals to a vacuum suction filter in which a metal sinter plate acted as filtration element. Every 24 h the filter-moist material was separated off, washed once with drinking water and air-dried in a thin layer. The crystallites had a mean particle diameter of 480 μm and exhibited a loss on drying of 12.1%. Over the running time of the plant of two weeks, this approached the steady state and the amount produced reached an amount roughly of 0.76 g/min of creatine monohydrate. The content of the unwanted impurity dicyandiamide detected by HPLC in the purified creatine monohydrate was 30 ppm.

EXAMPLE 2

In a 2000 ml jacketed flat-flange flask, 1880 ml of drinking water were heated to 50° C. and solid creatine monohydrate was added up to the solubility limit. 700 g of anhydrous creatine (residual moisture less than 0.1%) were then added a little at a time distributed over 10 h in the form of roughly 4 μm particles which had been previously intimately mixed with 7 g of anhydrous sodium sulfate. Sodium sulfate is a potential impurity of creatine synthesis. After further stirring overnight at room temperature, the roughly 30% strength suspension was run off to a vacuum suction filter; the filter was then washed once with drinking water at 50° C. and the residue was air-dried in a thin layer. The crystallites exhibited a loss on drying of 12.2% and contained a residual sulfate content of 0.05% as determined by ion chromatography.

We claim:

1. A process for purifying creatine in which the creatine to be purified in the form free of water of crystallization is introduced into a saturated aqueous solution of creatine monohydrate, in which the creatine free of water of crystallization is dissolved with hydration, crystals of creatine monohydrate precipitate from the aqueous solution and these are separated off from the aqueous solution.

2. A process as claimed in claim 1, wherein the saturated aqueous creatine monohydrate solution is prepared in situ by introducing the creatine free of water of crystallization into water or a mixture of water with a water-miscible organic solvent.

3. A process as claimed in claim 1, wherein the creatine free of water of crystallization is introduced into an aqueous suspension of creatine monohydrate seed crystals.

4. A process as claimed in claim 3, wherein the aqueous suspension of creatine monohydrate seed crystals is charged into a reactor into which water, or a mixture of water with a water-miscible organic solvent, and creatine free of water of crystallization are introduced continuously in parallel and a suspension of creatine monohydrate crystals is discharged continuously.

5. A process as claimed in claim 1, wherein the creatine monohydrate crystals are separated from the aqueous solution by filtration or centrifugation.

6. A process as claimed in claim 1, wherein the form which is free of water of crystallization of the creatine to be purified is obtained by drying creatine monohydrate.

7. A process as claimed in claim 1, wherein a mean crystal size of the resultant creatine monohydrate of from 200 to 600 μm is set by selecting the temperature and residence time.

8. A process for preparing creatine monohydrate, in which a) sarcosine is reacted in an aqueous medium with a guanylating agent, crude creatine monohydrate separating out, b) the crude creatine monohydrate is separated off from the aqueous medium, c) the crude creatine monohydrate which is separated off is, if appropriate, washed with a wash liquid, d) the crude creatine monohydrate is converted into creatine free of water of crystallization, e) the creatine free of water of crystallization is introduced into a saturated aqueous creatine monohydrate solution, the creatine free of water of crystallization being dissolved with hydration and creatine monohydrate crystals separating out, f) the creatine monohydrate crystals are separated off from the aqueous solution and the aqueous solution separated off is used at least in part as aqueous medium in step a) and/or as wash liquid in step c).

* * * * *